(12) United States Patent
Chen et al.

(10) Patent No.: US 11,612,040 B2
(45) Date of Patent: Mar. 21, 2023

(54) DYNAMIC LIGHT CONTROL METHOD FOR CONTROLLING AT LEAST ONE ILLUMINATION PARAMETER

(71) Applicant: LEDVANCE GmbH, Garching bei Munchen (DE)

(72) Inventors: Shaoping Chen, Shenzhen (CN);
Dandan Hou, Shanghai (CN);
Huaming Chen, Shenzhen (CN);
Yandan Lin, Shanghai (CN)

(73) Assignee: LEDVANCE GMBH, Garching bei Munchen (DE)

( * ) Notice: Subject to any disclaimer, the term of this patent is extended or adjusted under 35 U.S.C. 154(b) by 0 days.

(21) Appl. No.: 17/179,993

(22) Filed: Feb. 19, 2021

(65) Prior Publication Data

US 2021/0267037 A1 Aug. 26, 2021

(30) Foreign Application Priority Data

Feb. 20, 2020 (CN) .......................... 202010105522.3

(51) Int. Cl.
*H05B 47/16* (2020.01)
*A61M 21/00* (2006.01)

(52) U.S. Cl.
CPC ............. *H05B 47/16* (2020.01); *A61M 21/00* (2013.01); *A61M 2021/0044* (2013.01)

(58) Field of Classification Search
CPC ...... H05B 47/16; H05B 47/165; A61M 21/00; A61M 2021/0044; A61M 21/02; A61M 2205/50; A61M 2205/587; Y02B 20/40
See application file for complete search history.

(56) References Cited

U.S. PATENT DOCUMENTS

| 9,635,732 | B2 * | 4/2017 | Herremans | ............ H05B 47/16 |
| 9,642,209 | B2 * | 5/2017 | Eisele | .................... H05B 45/22 |
| 2013/0141018 | A1 * | 6/2013 | Kamii | .................... H05B 47/10 |
| | | | | 315/360 |

FOREIGN PATENT DOCUMENTS

| CN | 102986299 A | 3/2013 |
| WO | 2012011008 A1 | 1/2012 |

* cited by examiner

*Primary Examiner* — Daniel D Chang
(74) *Attorney, Agent, or Firm* — Hayes Soloway PC

(57) ABSTRACT

A dynamic light control method for controlling at least one adjustable illumination parameter at a target location has been suggested. The method comprises setting the value of at least one adjustable illumination parameter at a first predetermined level, maintaining the value of the at least one adjustable illumination parameter at the first predetermined level for a first predetermined time period, varying the value of the at least one adjustable illumination parameter from the first predetermined level to a second predetermined level, maintaining the value of the at least one adjustable illumination parameter at the second level for a second predetermined time period, and varying the value of the at least one adjustable illumination parameter from the second level to a third predetermined level, wherein the varying the at least one adjustable illumination parameter comprises monotonously varying the at least one adjustable illumination parameter with a predefined maximum variation rate.

20 Claims, 3 Drawing Sheets

DYNAMIC LIGHT CONTROL METHOD FOR CONTROLLING AT LEAST ONE ILLUMINATION PARAMETER

CROSS-REFERENCE TO RELATED APPLICATIONS AND PRIORITY

This patent application claims priority from Chinese Patent Application No. CN 202010105522.3 filed Feb. 20, 2020, which is incorporated by reference herein in its entirety.

TECHNICAL FIELD

The technical field of the present application generally relates light control methods. In particular, the present disclosure relates to a method for controlling at least one illumination parameter.

BACKGROUND

It is known that light can affect humans in various ways. The light used for illumination purposes, for instance, can influence concentration ability, work performance, as well as alertness, circadian rhythm shift and emotion of humans. Illumination systems with two illumination modes for helping people to switch between different states are known as well, in which a first illumination mode may serve for maintaining high alertness, while a second illumination may serve for facilitating human relaxation. It is further known that pulsed lighting can be used, in order to increase human alertness and concentration ability. A pulsed lighting, however, as well as switching from one more into another can cause irritation and thus deteriorate the life quality as well as the overall performance of humans.

SUMMARY

An object of the present application is to provide a light control method for controlling at least one illumination parameter which can improve human performance and reduce irritation caused by light.

According to a first aspect, a dynamic light control method for controlling at least one illumination parameter at a target location is provided. The target location can be, in particular, an expected or intended eye location of a human, e.g. worker or machine operator, whose performance is to be improved. The method can be carried out by means of any controllable luminaire or adjustable light source, in particular of an illumination system configured to set and dynamically vary at least one illumination parameter at the target location. The suitable illumination systems may for instance comprise one or more controllable light sources for providing a dimmable light with variable illumination parameters, such as illuminance and color temperature or correlated color temperature (CCT) of the light at the target location.

According to the method, during a first cycle or control cycle, the following steps are carried out: setting the value of the at least one illumination parameter at a first predetermined level, maintaining the value of the at least one illumination parameter at the first predetermined level for a first predetermined time period, varying the value of the at least one adjustable illumination parameter from the first predetermined level to a second predetermined level, maintaining the value of the at least one adjustable illumination parameter at the second predetermined level for a second predetermined time period and varying the value of the at least one adjustable illumination parameter from the second predetermined level to a third level, wherein the varying the at least one adjustable illumination parameter comprises essentially monotonously varying the at least one illumination parameter with a predetermined maximum variation rate.

The first predetermined level, the second predetermined level and third predetermined level may be predetermined or controlled according to control target, in particular, by the user of a light control device of the illumination system, for instance by selecting appropriate user settings.

The change in the value of the at least one illumination parameter at the target location can help to change the emotional and/or physical state of the human whose eyes are exposed to the illumination. By influencing the alertness or relaxedness of humans, e.g. machine operators or office workers, their overall performance can be improved. Thereby, due to the monotonous variation of the parameter with a predetermined maximum rate, irritations or inconveniences caused by the changes in the illumination parameters can be avoided or reduced.

The first predetermined level and the third predetermined level may be selected from a first predetermined range, while the second predetermined level may be selected from a second predetermined range. The first parameter range and the second parameter range can be, in particular, selected depending on the desired effect the illumination is supposed to cause, while the specific parameter levels within the respective ranges can be selected to adjust the strength of the effect. Thus, the selection of the parameter levels with the respective ranges can serve as a fine tuning or adjustment of the magnitude of the desired effect.

The first predetermined time period may be selected from a first predetermined time period range and the second predetermined time period may be selected form a second predetermined time period range. The selection of the time period ranges and the time periods within the ranges can be used to achieve the best performance depending on specific tasks.

The first predetermined time period range may extend from 1 min to 60 min and the second predetermined time period range may be less than 60 min. In particular, the duration of the whole cycle may be approximately one hour. In some embodiments the first time period has a duration of approximately 45 minutes equal to one "academic hour". Such time interval is particularly suitable for mental activities where high concentration is required.

Prior to the setting the at least one illumination parameter at the first predetermined level, in particular, at a start stage, the at least one illumination parameter may be gradually varied from an initial level to the first predetermined level. The duration of this start stage or initial phase can be chosen such that the human eye has enough time to gradually adjust to the first parameter level.

The first control cycle may be followed by at least one subsequent control cycle. By providing a plurality of control cycles the human state can be conditioned for a longer time period, such that overall performance for a longer time period, e.g. over long working hours, can be improved.

The first predetermined level, second predetermined level and/or third predetermined level may vary from cycle to cycle. Thereby, the parameter level settings can differ from cycle to cycle, such that the illumination influence can be modulated over the time in accordance to specific requirements or user's preferences.

The third predetermined level of each cycle may serve as the first predetermined level of each subsequent cycle. By equalizing the third parameter level of a cycle with the first parameter level of respective subsequent cycle, it can be ensured that no abrupt cycle-to-cycle jump takes place. Thus, a smooth operation of the illumination system can be achieved, which is particularly gentle to the human eye.

In some embodiments, the at least one illumination parameter comprises vertical illuminance at the target location. Vertical illuminance can serve for characterizing the light intensity to which the human eye is exposed under normal working conditions, e.g. in a production hall or office environment, as the case may be. By varying the vertical illuminance at the target location, the person's state can be efficiently affected such that his or her vigilance and performance is improved.

In some embodiments, the first predetermined range for vertical illuminance may extend from 1000 lx to 3000 lx and the second predetermined range may extend from 150 lx to 800 lx. These ranges for vertical illuminance are suitable for switching a person from alert state to relaxation state and back. By purposefully alternating the alert state and the relaxation state, a substantial performance improvement can be achieved.

The change rate of the vertical illuminance may be less than 2.5 lx/s. By keeping the change rate of vertical illuminance below 2.5 lx/s, irritations caused by changes in the vertical illuminance can be avoided or reduced.

In some embodiments, a temperature changing mode of the method is implemented. Therein the at least one illumination parameter comprises light color temperature, in particular, at the target location. Color temperature of light can have a strong influence on emotional state of humans. In particular, high color temperature of illumination light can help to increase alertness and concentration capacity, while low color temperature of illumination light can help to relax and regenerate after an intense mental effort. Thus, by purposefully alternating color temperature, a substantial improvement in human performance can be achieved.

The first predetermined range for color temperature may extend from 5000 K to 6500 K, and the second parameter range for color temperature may extend from 3000 K to 50000 K. Alternating between these color temperature ranges can lead to alternating emotional state such that an overall improvement in human performance is achieved.

The change rate of the color temperature is less than 50 K/s. In particular, the change may take continuously along the Planck's locus in an essentially continuous manner. By keeping the change rate of color temperature below 50 K/s, irritations caused by changes in the vertical illuminance can be avoided or reduced.

In some embodiments, the at least one adjustable illumination parameter comprises two or more parameters. For instance, the at least one adjustable illumination parameter may comprise both, vertical illuminance and color temperature. The vertical illuminance and color temperature may change at the same time.

In some embodiments the illuminance and color temperature can be adjusted independently such that illuminance changing mode and color temperature changing mode may be implemented jointly or independently, depending on specific requirements. The joint or synchronous operation of the two modes can be used, in particular, to maximize the effect of the dynamical lighting on humans, while the independent or asynchronous operation of these two modes can be used in cases when additional factors, like circadian rhythm or jet lag, are to be taken into account.

In the following description, details are provided to describe the embodiments of the present specification. It shall be apparent to one skilled in the art, however, that the embodiments may be practiced without such details.

DETAILED DESCRIPTION

Figure 1:
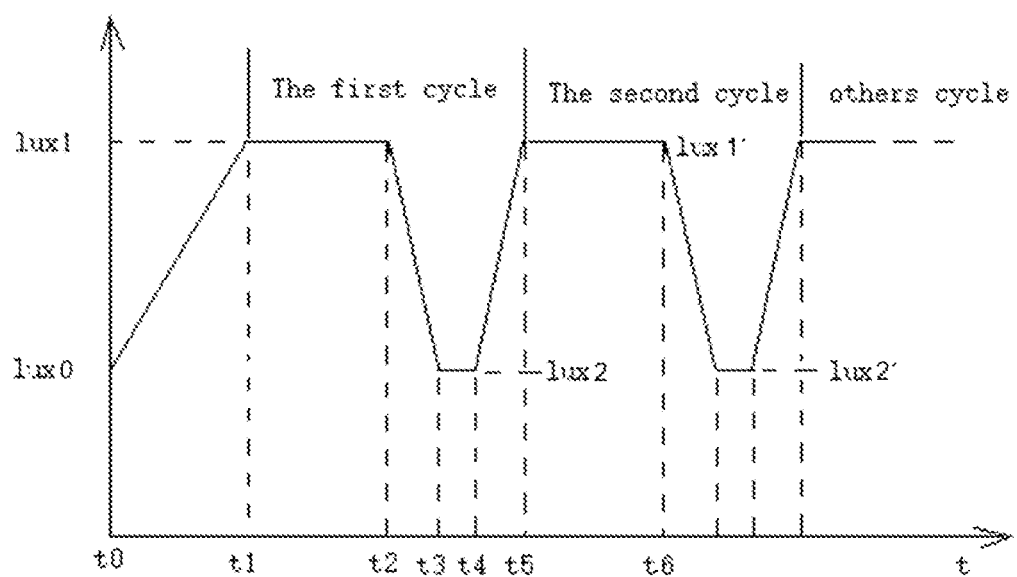
FIG. 1 shows schematically a time dependence of vertical illuminance, according to one embodiment.

FIG. 1 shows schematically a time dependence of vertical illuminance according to one embodiment, wherein time (x-axis) and vertical illuminance (y-axis) are shown in arbitrary units. FIG. 1 illustrates, in particular, how the vertical illuminance varies over time on the example of two consecutive control cycles. The method, however, is not limited to two cycles. It can be also implemented in a single control cycle or in a plurality of cycles, depending on embodiment.

At the beginning, starting from time point t0, the vertical illuminance increases monotonously from the initial level lux0 to the first level lux1. After that, in the first cycle, starting at the time point t1, the vertical illuminance is kept constant during a first time period lasting till time point t2. From time point t2 until time point t3, the vertical illuminance decreases monotonously to a second level lux2 and remains constant at this level until time point t4 after which it increases again to reach the third level of vertical illuminance lux1' at time point t5. At time point t5 and at the third level of the third vertical illuminance lux', the first cycle ends, and the second cycle starts.

The temporal variation of vertical illuminance in the second cycle shows essentially the same character as in the first cycle, whereby the third level of the vertical illuminance (lux1') of the first cycle serves as the first level of the vertical illuminance of the second cycle.

The first level lux1' and the second level lux2' of the second cycle, may generally differ from the first level lux1 and the second level lux2 of the first cycle. The first time period corresponding to the time interval between time points t1 and t2 may lie in the range from 1 min to 60 min and the second time interval between time points t3 and t4 may be 60 min or less. The first level of vertical illuminance lux1 may lie in the range from 1000 lx to 3000 lx and the second level of the vertical illuminance may lie in the range from 150 lx to 800 lx. The rate of illuminance change may be less than 2.5 lx/s.

Although both cycles, as well as any further cycle may have essentially the same character, the cycle parameters, like first time period, second time period, first vertical illuminance level and second vertical illuminance level may differ from cycle to cycle. The ranges of respective parameters may remain the same for different cycle.

The first predetermined level of vertical illuminance lux1, the second level of vertical illuminance lux2 as well as the time duration of the first time period (t2-t1) and the second time period (t4-t3), as well as the respective parameter ranges, may be predetermined by the user in a light control device, in particular, by selecting appropriate user settings.

In the embodiment of FIG. 1, the change of the vertical illuminance during the transition between different illuminance levels is linear. However, in other embodiments, the change of the vertical illuminance may be a parabolic time function or other monotonous function. In particular, the change may depend on the absolute value of the illuminance, such that for low illuminance values, the change rate is lower and for high illuminance values, the change rate is higher, as in the case of a parabolic time function with positive second derivative. In such way, irritations caused by variation of illuminance can be avoided or reduced.

Figure 2:
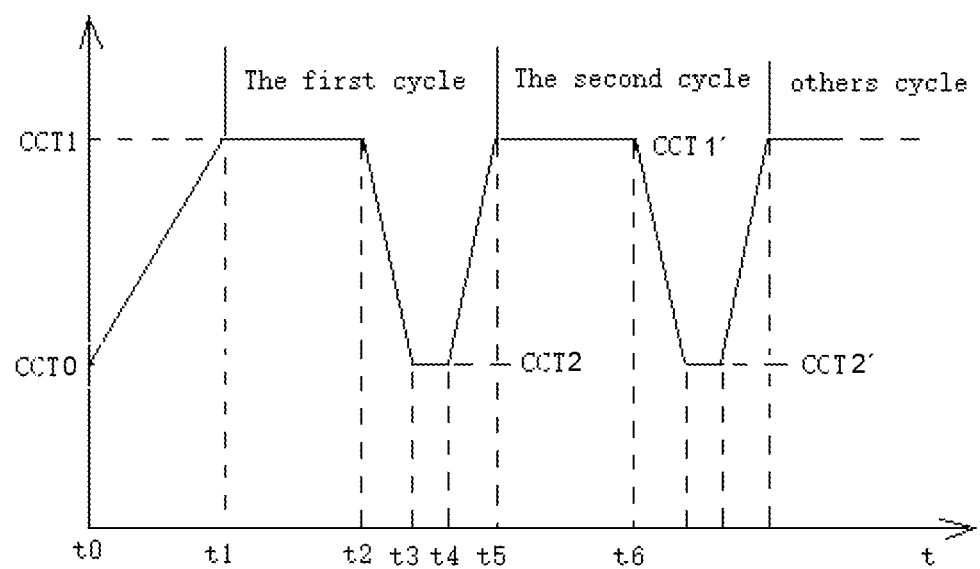
FIG. 2 shows schematically a time dependence of color temperature, according to one embodiment.

FIG. 2 shows schematically a time dependence of color temperature, according to one embodiment, wherein time (x-axis) and color temperature (y-axis) are shown in arbitrary units. The temporal variation of the color temperature or correlated color temperature (CCT) shows essentially the same pattern as the temporal variation of the color temperature shown in FIG. 1. FIG. 2 shows, in particular, how the color temperature varies over time on the example of two consecutive control cycles. The method, however, is not limited to two cycles. It can be also implemented in a single cycle or in a plurality of cycles, depending on embodiment.

At the beginning, at time point t0, the color temperature increases monotonously from the starting value CCT0 to the first level CCT1. After that, in the first cycle, starting at time point t1, the color temperature is kept constant during a first time period lasting until time point t2. From time point t2 until time point t3, the color temperature decreases monotonously to a second level CCT2 and remains constant at that level until time point t4. At time point t4, color temperature starts increasing again to reach the third level of color temperature CCT1' at time point t5. At time point t5 and at the third level of the third color temperature CCT', the first cycle ends, and the second cycle starts.

The temporal variation of color temperature in the second cycle shows essentially the same pattern as in the first cycle, whereby the third level of the color temperature (CCT1') of the first cycle serves as the first level of the color temperature of the second cycle. The first level CCT1' and the second level CCT2' of the second cycle, may generally differ from the first level CCT1 and the second level CCT2 of the first cycle.

The first time period corresponding to the time interval between time points t1 and t2 may lie in the range from 1 min to 60 min and the second time interval between time points t3 and t4 may be 60 min or less. The first level of color temperature CCT1 may lie in the range from 5000 K to 6500 K and the second level of the color temperature may lie in the range from 3000 K to 5000 K. The rate of change of color temperature may be less than 50 K/s.

Although both cycles, shown in FIG. 2, as well as any subsequent cycle may have essentially the same character, the cycle parameters, like first time period, second time period, first color temperature level and second color temperature level may differ from cycle to cycle. The parameter ranges for difference cycle may remain the same.

The first predetermined level of color temperature CCT1, the second level of color temperature CCT2, the time duration of the first time period (t2-t1) and the second time period (t4-t3) as well as the respective parameter ranges may be predetermined by the user in a light control device, in particular, by selecting appropriate user settings.

In the embodiment of FIG. 2, the change of color temperature during the transitions between different color temperature levels is linear. However, in other embodiments, the change of the color temperature may be a parabolic time function or other monotonous function. In particular, the change may depend on the absolute value of the color temperature, such that for low color temperature values, the change rate is lower and for high color temperature values, the change rate is higher, e.g. in the case of a parabolic time function with positive second derivative. In such way, irritations caused by variation of color temperature can be avoided or reduced. In some embodiments the change rate of color temperature is a non-linear function of color temperature, taking into account the human perception of color temperature changes, in particular based on the movement of the white point along the Planck's locus, such that the perceived color change rate is essentially constant.

Figure 3:
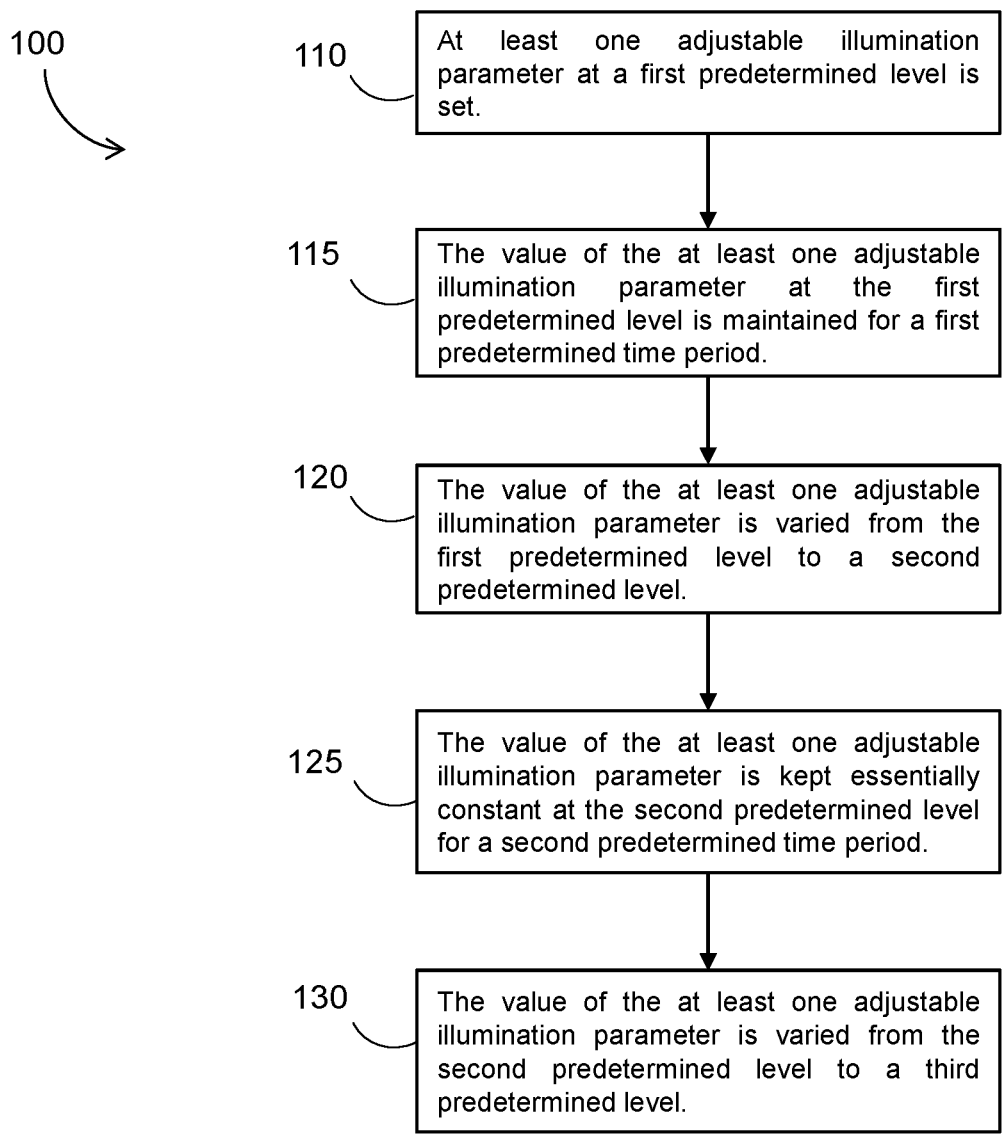
FIG. 3 shows a flow chart of a method according to one embodiment.

FIG. 3 shows a flow chart of a control cycle of a light control method according to an embodiment. The method can be carried out by an illumination system with at least one adjustable illumination parameter at a target location, i.e. measurable at the target location. In particular, such an illumination system may comprise at least one adjustable light source, with a driver for driving the light source and a control unit for controlling the driver of the adjustable light source. The control unit may comprise a memory unit, for saving data and computer-readable instructions, as well as a processor configured to read out the computer-readable memory and carry out the computer-readable instructions. The control unit may further comprise one or more control interfaces for controlling the driver of the adjustable light source by means of the control unit. The illumination system may also comprise one or more user interfaces for inputting user commands and/or adjusting user settings. The computer-readable instructions may in particular comprise computer-readable instructions to carry out the steps of different embodiments of the present method.

According to the flow chart 100 of the embodiment of FIG. 3, in the first step 110, at least one adjustable illumination parameter at a first predetermined level is set. In step 115, the value of the at least one adjustable illumination parameter at the first predetermined level is maintained for a predetermined time period. In step 120, the value of the at least one adjustable illumination parameter is varied from the first predetermined level to a second predetermined level. In step 125, the value of the at least one adjustable illumination parameter is kept essentially constant at the second level for a second predetermined time period. Further, in step 130, the value of the at least one adjustable illumination parameter is varied from the second level to a third predetermined level. With step 130 ends the first cycle. The predetermined parameter levels and the time periods may be selected from respective predetermined ranges.

In some embodiments, the method comprises two or more control cycles each comprising steps similar to the steps 110, 125, 120, 125 and 130 described above. The predetermined parameter levels and the predetermined time periods may differ from cycle to cycle, while corresponding parameter level ranges and the time period ranges may be the same for different cycles.

In some embodiments, in an initial phase, i.e. prior to carrying out the first cycle, prior to the setting the at least one illumination parameter at the first predefined level, the at least one illumination parameter is gradually varied from an initial level to the first level.

In some embodiments, the at least one illumination parameter comprises vertical illuminance at the target location. Vertical illuminance at the target location can, in particular, serve for characterizing the light intensity to which the human eye is exposed under normal working conditions. By varying the vertical illuminance at the target location, the person's state can be affected such that his or her vigilance and performance is improved. In some embodiments, the first predetermined level is selected from a range between 1000 lx and 3000 lx and the second level is selected from a range between 150 lx and 800 lx. These ranges of vertical illuminance are suitable for switching a person from an alert state (at higher values of vertical illuminance) to a relaxation state (at lower values of vertical illuminance) and back. By purposefully alternating the alert state and the relaxation state, a substantial performance improvement can be achieved. The change rate of the vertical illuminance, in particular between the first time period and the second time period as well as in the initial phase, may be less than 2.5 lx/s. By keeping the change rate of vertical illuminance below 2.5 lx/s, irritations caused by changes in the vertical illuminance can be avoided or reduced.

In some embodiments, the at least one illumination parameter comprises light color temperature, in particular, color temperature of the illumination light at the target location. Color temperature of light can have a strong influence on emotional state of humans. In particular, high color temperature can help to increase alertness and concentration capacity, while low color temperature of illumination light can help to relax and regenerate after an intense mental activity. Thus, by purposefully alternating color temperature, a substantial improvement in performance can be achieved. The first predetermined range for color temperature may extend from 5000 K to 6500 K and the second parameter range for color temperature may extend from 3000 K to 5000 K. Alternating between these color temperature ranges can lead to alternating emotional state such that an overall improvement in human performance is achieved. These ranges of color temperature are suitable for switching a person from an alert state (at higher values of color temperature) to a relaxation state (at lower values of color temperature) and back. By purposefully alternating the alert state and the relaxation state, a substantial performance improvement can be achieved. The change rate of color temperature, in particular between the first time period and the second time period as well as in the initial phase, may be less than 50 K/s. By keeping the change rate of color temperature below 50 K/s, irritations caused by changes in the color temperature can be avoided or reduced.

In some embodiments, the at least one adjustable illumination parameter comprises two or more parameters. For instance, the at least one adjustable illumination parameter may comprise both, vertical illuminance and color temperature, wherein the vertical illuminance and color temperature may change at the same time.

In some embodiments the illuminance and color temperature can be adjusted independently such that illuminance changing mode and color temperature changing mode may be implemented jointly or independently. The joint or synchronous operation of the two modes can be used, in particular, to maximize the effect of the dynamical lighting on humans, for instance to reach peak performance in specific time periods.

While at least one exemplary embodiment has been presented in the foregoing detailed description, it should be appreciated that a vast number of variations exists. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments.

The invention claimed is:

1. A dynamic light control method for controlling at least one adjustable illumination parameter at a target location, wherein during a first control cycle the following steps are carried out:
    setting the value of the at least one adjustable illumination parameter at a first predetermined level;
    maintaining the value of the at least one adjustable illumination parameter constant at the first predetermined level for a first predetermined time period;
    varying the value of the at least one adjustable illumination parameter from the first predetermined level to a second predetermined level, wherein the first predetermined level is greater than the second predetermined level;
    maintaining the value of the at least one adjustable illumination parameter constant at the second predetermined level for a second predetermined time period; and
    varying the value of the at least one adjustable illumination parameter from the second predetermined level to a third predetermined level, wherein varying the value of the at least one adjustable illumination parameter comprises monotonously varying the at least one adjustable illumination parameter with a predefined maximum variation rate.

2. The method of claim 1, wherein the first predetermined level and the third predetermined level are selected from a first predetermined range, and the second predetermined level is selected from a second predetermined range.

3. The method of claim 2, wherein the at least one adjustable illumination parameter comprises vertical illuminance.

4. The method of claim 3, wherein:
    the first predetermined range for the vertical illuminance extends from 1000 lx to 3000 lx; and
    the second predetermined range for the vertical illuminance extends from 150 lx to 800 lx.

5. The method of claim 3, wherein the predefined maximum variation rate of the vertical illuminance is less than 2.5 lx/s.

6. The method of claim 2, wherein the at least one adjustable illumination parameter comprises light color temperature.

7. The method of claim 6, wherein:
    the first predetermined range for the light color temperature extends from 5000 K to 6500 K; and
    the second predetermined range for the light color temperature extends from 3000 K to 5000 K.

8. The method of claim 6, wherein the predefined maximum variation rate of the light color temperature is less than 50 K/s.

9. The method of claim 1, wherein the first predetermined time period is selected from a first predetermined time period range, and the second predetermined time period is selected from a second predetermined time period range.

10. The method of claim 9, wherein the first predetermined time period range extends from 1 min to 60 min and the second predetermined time period range is less than 60 min.

11. The method of claim 1, wherein prior to setting the value of the at least one adjustable illumination parameter at the first predefined level, the at least one adjustable illumination parameter is gradually varied from an initial level to the first predetermined level.

12. The method of claim 1, wherein the first control cycle is followed by at least one subsequent control cycle.

13. The method of claim 12, wherein at least one of the first predetermined level, the second predetermined level, and the third predetermined level varies from cycle to cycle.

14. The method of claim 12, wherein the third predetermined level of each cycle serves as the first predetermined level of each subsequent cycle.

15. The method of claim 1, wherein the third predetermined level is greater than the second predetermined level.

16. The method of claim 15, wherein the first predetermined level and the third predetermined level are substantially equivalent.

17. The method of claim 1, wherein the first predetermined time period is greater than the second predetermined time period.

18. The method of claim 1, wherein the predefined maximum variation rate is held constant over at least one of:
   an entire time period of transition from the first predetermined level to the second predetermined level; and
   an entire time period of transition from the second predetermined level to the third predetermined level.

19. The method of claim 1, wherein:
   the at least one adjustable illumination parameter comprises both vertical illuminance and light color temperature; and
   the vertical illuminance and the light color temperature are varied simultaneously.

20. The method of claim 1, wherein:
   the at least one adjustable illumination parameter comprises both vertical illuminance and light color temperature; and
   the vertical illuminance and the light color temperature are varied independently.

* * * * *